United States Patent [19]

Holian et al.

[11] Patent Number: 5,456,248
[45] Date of Patent: Oct. 10, 1995

[54] SURGICAL SMOKE EVACUATOR

[75] Inventors: Steven E. Holian, Moreno Valley Ranch; Donald R. Reiterman, Hemet; Richard J. Greff, Yorba Linda; Ronald E. Thomas, Alta Loma, all of Calif.

[73] Assignee: Stackhouse, Inc., Riverside, Calif.

[21] Appl. No.: 960,934

[22] Filed: Oct. 14, 1992

[51] Int. Cl.[6] .............................. A62B 7/10; A62B 19/00; A62B 23/02
[52] U.S. Cl. ................................ 128/205.12; 128/205.27; 128/205.29
[58] Field of Search .................... 128/205.12, 205.19, 128/205.27, 205.28, 205.29, 910, 909; 55/74, 75, 97, 98, 328, 383, 389, 422, 490, DIG. 30, DIG.31, 483, 485, 486; 96/121, 129, 131, 133, 136, 138, 147, 151; 95/286, 287

[56] References Cited

U.S. PATENT DOCUMENTS

| | | | |
|---|---|---|---|
| 1,843,446 | 2/1932 | Drager | 96/131 |
| 2,345,530 | 3/1944 | Connell | 128/205.28 |
| 2,701,030 | 2/1955 | Hazelton | 128/205.29 |
| 2,837,413 | 6/1958 | Hay | 128/205.28 |
| 3,088,810 | 5/1963 | Hay | 128/205.28 |
| 3,240,567 | 3/1966 | Caparreli et al. | 128/205.28 |
| 3,738,360 | 6/1973 | Dryden | 128/909 |
| 3,830,632 | 8/1974 | Guzay | 128/205.28 |
| 4,055,173 | 10/1977 | Knab . | |
| 4,082,092 | 4/1978 | Foster . | |
| 4,487,606 | 12/1984 | Leviton et al. . | |
| 4,576,616 | 3/1986 | Mottram et al. | 128/205.27 |
| 4,619,672 | 10/1986 | Robertson . | |
| 4,642,128 | 2/1987 | Solorzano . | |
| 4,701,193 | 10/1987 | Robertson . | |
| 4,826,513 | 5/1989 | Stackhouse et al. | 96/131 |
| 4,963,134 | 10/1990 | Backschieder . | |
| 4,986,839 | 1/1991 | Wertz et al. . | |
| 5,108,474 | 4/1992 | Riedy et al. | 55/486 |
| 5,118,330 | 6/1992 | Gielow et al. | 55/486 |
| 5,174,798 | 12/1992 | Luby | 96/131 |

FOREIGN PATENT DOCUMENTS

| | | | |
|---|---|---|---|
| 769248 | 6/1934 | France | 128/205.29 |
| 2029414 | 12/1971 | Germany | 128/205.29 |
| 2856503 | 7/1979 | Germany | 128/205.28 |
| 111985 | 10/1965 | Netherlands | 128/205.29 |

*Primary Examiner*—Kimberly L. Asher
*Attorney, Agent, or Firm*—Richard L. Myers

[57] ABSTRACT

A surgical smoke evacuator includes a housing and means defining an air flow channel through the housing. At least one filter having a longitudinal axis is disposed in the air flow channel with portions of the housing defining an inlet for receiving the filter and a filter cavity for receiving the filter in the air flow channel. Tabs on the filter and associated guide slots on the housing, guide the filter along a circuitous path between the inlet and filter cavity during loading and unloading of the filter. This path includes axial portions which facilitate axial filter movement and angular portions which facilitate angular filter movement relative to the housing.

10 Claims, 6 Drawing Sheets

SURGICAL SMOKE EVACUATOR

BACKGROUND OF THE INVENTION

1. Field of the Invention

This invention relates generally to vacuum and filter apparatus and more specifically to such apparatus adapted to receive, filter and purify surgical smoke.

2. Discussion of the Prior Art

Surgical smoke typically results from use of electrosurgical devices and lasers for cutting, cauterizing or otherwise ablating body tissue. Particularly if the tissue is diseased in any way, the surgical smoke may contain infectious particles which render the smoke hazardous to the patient, surgeon and supporting staff. In the past, surgical smoke evacuators have typically been stand alone devices including replaceable filters, and a control panel which is operable to control the speed of evacuation and also to time the amount of use attributed to the various removable filters. These filters will typically include a first stage prefilter for the removal of coarse particles, a second stage filter for removing fine particles, and a third stage charcoal filter for removing odors. Each of these filters is disposed within an air flow channel which begins with an intake tube and typically ends with a vacuum motor which produces the desired air flow.

The primary filtration of these smoke evacuators is typically provided by the second filter which has a relatively large surface area. In order to maintain an effective air flow channel, it is important that this filter be properly aligned and sealed to prevent air leaks. This is difficult to achieve in the case of the relatively large second filter, particularly if the filter is mounted within a closed housing where the filter can not be reached to achieve proper alignment.

Since the various filters are disposable, and may be contaminated by the particles filtered from the smoke, one must exercise considerable care in the handling of these devices. The filters of the past have relatively large planar surfaces which are usually contacted during the disposal process. When these surfaces are contaminated with hazardous particles, they represent a significant risk to the person disposing of the filter.

SUMMARY OF THE INVENTION

In accordance with the present invention, a prefilter and primary filter are provided with mating projections which are of particular advantage to a person disposing of the filters. These projections extend from planar surfaces which may be contaminated by the filtered smoke. The projections, which are isolated from contamination, are sufficient in number and small enough in diameter that they prevent a person from contacting the contaminated planar surfaces. These projections have a telescoping relationship which tends to channel the smoke into areas between the projections which need not be contacted in the disposal process.

The primary filter of the present invention is configured so that it can be loaded and unloaded from the evacuator by contacting only one end of the filter. An alignment system cooperates between the housing of the evacuator and the filter to guide the filter into a properly seated relationship within the air flow channel. This alignment system in a preferred embodiment includes a series of tabs on one of the filter and the housing which align with slots on the other of the filter and the housing to align the filter as it is loaded into and removed from the evacuator.

With the appropriate alignment and guidance, the filter can be engaged from only one end of the filter and brought into final alignment with the primary filter disposed in the flow path. In this ultimate position, a tab on the filter can be used to activate a delicate lever switch which clocks the total time of filter use. When the filter is placed in its operative position, the switch is closed to activate the clock wherever the evacuator is used. When the filter is replaced, the switch is opened and the clock is reset to zero for the new filter.

In one aspect of the invention, the evacuator includes a housing and means defining an air flow channel through the housing. At least one filter having a longitudinal axis is disposed in the air flow channel. Portions of the housing define an inlet for receiving the filter into the housing and a filter cavity for ultimately locating the filter in the air flow channel. Means cooperating between the filter and the housing guides the filter along a circuitous path between the inlet and filter cavity during loading and unloading of the filter. This path includes axial portions wherein the filter moves axially of the housing and angular portions wherein the filter moves angularly of the housing.

In another aspect of the invention a surgical smoke evacuator includes a housing and means defining an air flow channel for receiving the smoke to be evacuated. The filter disposed in the channel includes a plurality of tabs disposed on the filter. Filter alignment means having a fixed relationship with the housing define at least one alignment slot for receiving the tabs on the filter during loading and unloading of the filter.

These and other features and advantages of the invention will be more apparent with a description of preferred embodiments and reference to the associated drawings.

DESCRIPTION OF PREFERRED EMBODIMENTS

Figures 1, 2:
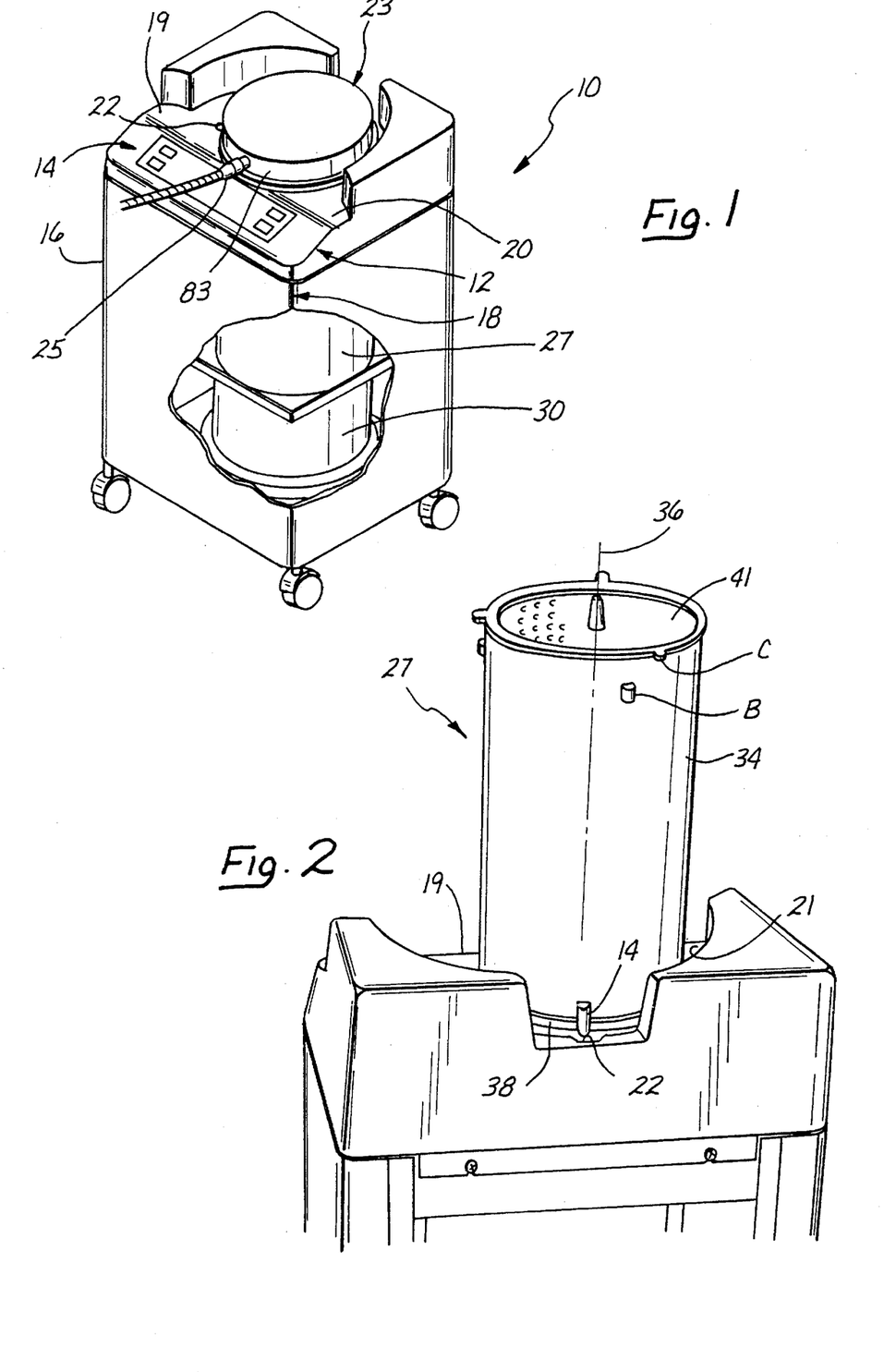
FIG. 1 is a perspective view of a surgical smoke evacuator of the present invention illustrating an intake hose, a prefilter and a housing defining a primary filter cavity.
FIG. 2 is a perspective view of a primary filter of the present invention disposed in a first alignment position.

A surgical smoke evacuator is illustrated in FIG. 1 and designated generally by the reference numeral 10. The evacuator 10 is particularly adapted for use in an operating room as a stand alone apparatus for removing, filtering and otherwise purifying smoke emanating from an operative site. This smoke typically results from electrosurgical or laser cutting, coagulating or ablating of tissue. The evacuator 10 includes an upstanding housing 12 having a front panel 14, a pair of side panels 16, 18 and a removable rear panel (not shown). The housing 12 includes a top panel 19 which has a top surface 20 and is adapted to receive various filters which purify the surgical smoke.

The top panel 19 forms a large hole 21 which is configured to receive the filter. Circumferential portions of this hole 21 include an alignment slot 22 discussed in greater detail below.

The filters of the evacuator 10 may include a prefilter 23, which receives the smoke through an intake hose 25, and a large primary filter 27, which is operatively disposed along an air flow path 29 and supported by a vacuum motor 30. The filters 23 and 27 are designed to remove undesirable particles from the surgical smoke. As that removal is accomplished, the filter 27 tends to clog and become increasingly ineffective for its intended purpose. For this reason, the primary filter 27 is designed with an effective life which is measured in terms of hours of use. When the filter has been spent, it is intended to be removed from the evacuator 10 and replaced by a new primary filter 27. It is this removal and replacement of the filter 27 which is of particular interest to the present invention.

The primary filter 27 of the present invention has generally cylindrical sidewalls 34 which define an axis 36. A bottom end wall 38 and top end wall 41 form with the sidewalls 34 an enclosure for various filter materials which form no part of the present invention. The top end wall 41 has a center post 42 which can be grasped by the user to facilitate loading the primary filter 27 in the evacuator 10. This wall 41 is specially configured to inhibit contact with contaminated surfaces as described in greater detail below.

In this particular embodiment, the primary filter 27 is provided with a plurality of tabs which are axially and radially displaced to facilitate alignment of the filter within the housing 12. These tabs are designated A, B, and C in FIG. 2 and comprise a tab group which function relative to an associated alignment slot, such as slot 22, in the top panel 19. Other tab groups similar to the tab group A, B, and C can be provided on the filter 27 for cooperative alignment with other alignment slots, similar to the slot 22.

In the illustrated embodiment, the alignment tab A is disposed in proximity to the bottom end wall 38. This tab A may be glued or otherwise adhered to the sidewall 34 of the filter 27, or formed integral with the bottom end wall 38. The alignment tab B is axially and angularly displaced from the tab A. It is typically adhered to the side wall 34 between the end walls 38 and 41. The alignment tab C is disposed in juxtaposition to the top end wall 41. As was the case with tab A, tab C can be fixed to the sidewall, or formed as an integral projection from the top end wall 41. In the illustrated embodiment, the tab C is axially and angularly displaced with respect to both the tabs A and B.

A person inserting the primary filter 27 into the evacuator 10 will typically grasp the center post 42 which extends axially upwardly from the top end wall 41. The bottom end wall 38 is then lowered into the evacuator 10. Since the user can neither reach nor see into the evacuator 10, the filter alignment apparatus within the housing is of particular interest to the present invention.

Initially, the tab A is inserted into the alignment slot 22 which permits the bottom end wall 38 to move downwardly through the hole 21. Continued insertion of the primary filter 27 in the axial direction will bring the tab B into contact with the top surface 20.

In order for the filter 27 to move further into the evacuator 10, the filter must be axially rotated until the tab B aligns with the slot 22. Once this alignment is achieved, further axial movement of the filter 27 will bring the alignment tab C into contact with the top surface 20. Again the filter 27 must be rotated until the tab C is aligned with the slot 22 where further axial movement brings the filter 27 into its final operative position. In this position, the filter 27 is disposed in the air flow path 29 in sealed communications with the vacuum motor 30.

Since the interior regions of the evacuator 10 can neither be seen nor reached by the user, the foregoing steps of the alignment process are the only steps which can be observed by the user. Axial movement of the filter 27 is accomplished by permitting gravity to draw the filter 27 downwardly into the evacuator 10. Angular movement of the filter 27 is accomplished by the user merely rotating the center post 42 as illustrated in FIG. 4.

Interiorly of the evacuator 10, alignment of the filter 27 is accomplished automatically. An alignment platform 50 is provided with a top surface 52 and portions which define an opening or hole 54 of sufficient size to receive the bottom end wall of the filter 27. Circumferential portions of the hole 54 include an alignment slot 56 which is displaced from the slot 22 by an axial distance corresponding to the axial distance separating the tabs A and C. The angular relationship of the slots 56 and 22 is also dependent upon the angular displacement of the tabs A and C.

Figure 4:
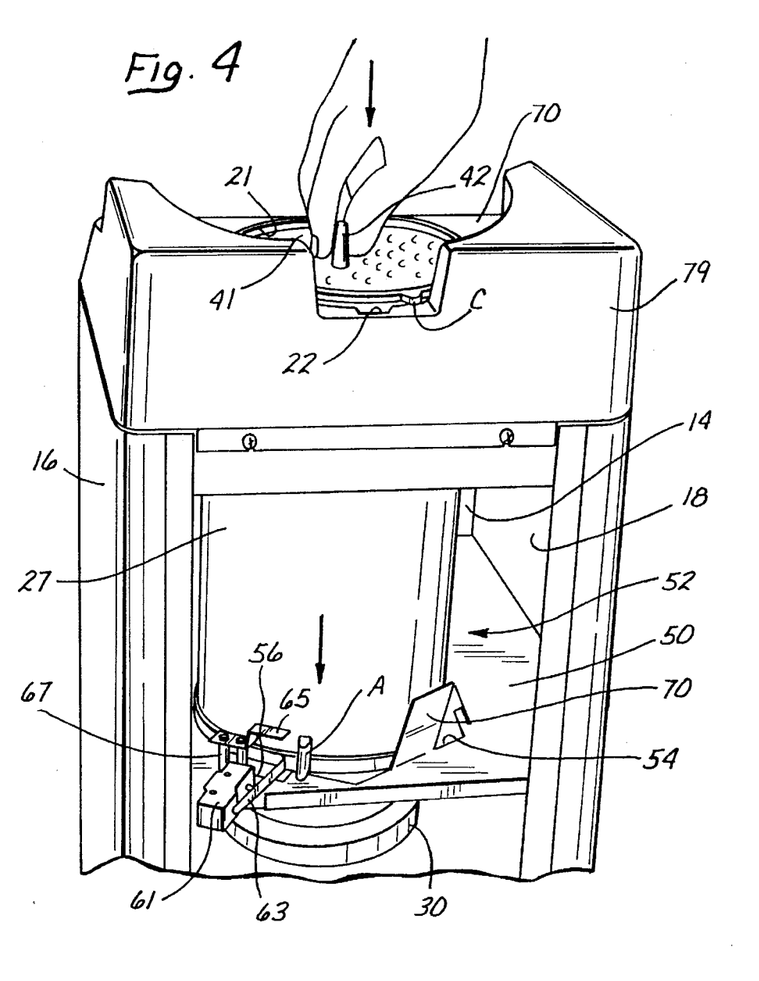
FIG. 4 is a perspective view of the primary filter of FIG. 2 disposed in a third alignment position.

A switch 61 can be mounted on the platform 50 and provided with a lever 63 which extends across the slot 56 as illustrated in FIG. 4. The switch 61 is normally biased to an open or "off" state wherein the lever extends outwardly from the switch, to the right in FIG. 4. When the lever 63 is moved inwardly of the switch 61, to the left in FIG. 4, the switch 61 is placed in its closed or "on" state.

A locking flange 65 can be fixed in an extended relationship with the platform 50 above the alignment slot 56. This locking flange 65 functions to retain the filter 27 it its operative position as described in greater detail below.

At least one and preferably two or three alignment flanges 70 can be provided to engage the bottom end wall 38 as the filter 27 is lowered into the evacuator 10. Preferably these alignment flanges 70 extend upwardly and outwardly from the surface 52 so that they function to guide or funnel the bottom end wall 38 into the hole 54.

Figure 3:
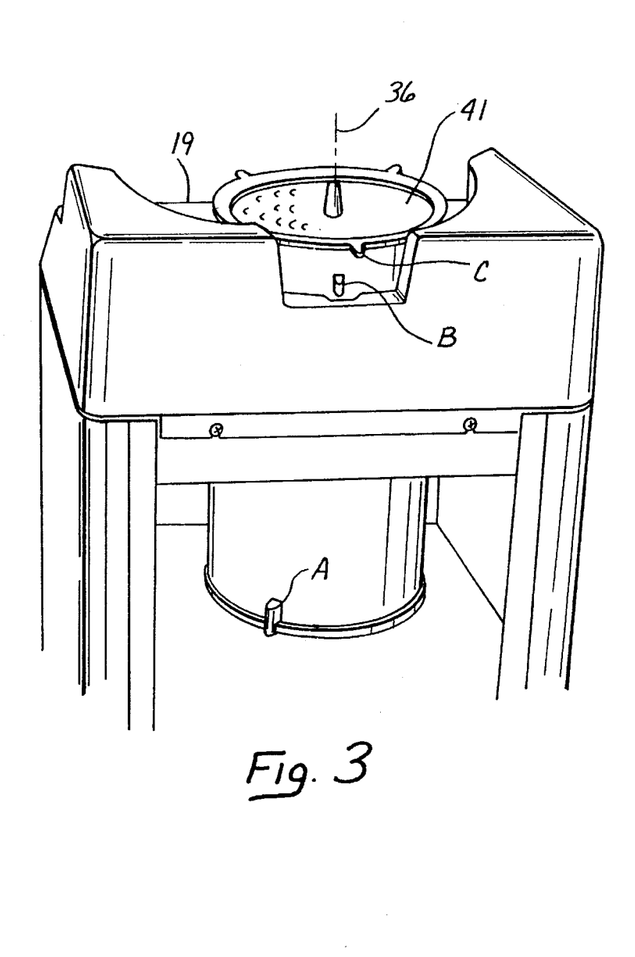
FIG. 3 is a perspective view of the primary filter of FIG. 2 disposed in a second alignment position.

Following the alignment procedure with respect to the bottom end wall 38 is somewhat more complex but need not be contemplated by the user who can neither see nor reach the interior of the housing 12. As the primary filter 27 is initially dropped into the hole 21 in the top panel 19, the tab A is aligned with the slot 22. From this first alignment position, illustrated in FIG. 2, the tab A is free to move axially with the filter 27 into the housing 12 until the tab B contacts the top surface 20 of the panel 19. By rotating the filter 27 the tab B can be angularly moved to register with the slot 22. This second position in the alignment process is illustrated in FIG. 3. The alignment of tab B with the slot 22 is of particular value to the present invention as it insures that the tab A does not contact either the locking flange 65 or the delicate switch 61 and lever, 63. It is desirable that the tabs A and B be sufficiently axially separated that the bottom end wall 38 is within the constraints of the flange 70 when the tab B registers with the slot 22 in the second alignment position. This will help maintain the axial alignment of the filter 27 as the angular rotation is imparted to the center post 42.

Once the tab B has been aligned with the slot 22 in the top panel 19, the filter 27 will again be free to drop further into the housing 20. This axial movement will continue until the tab C reached the surface 20 as illustrated in FIG. 4.

It is particularly desirable if the tabs A and C can be separated a distance such that the tab A contacts the surface 52 of the platform 50 at about the same time that the tab C contacts the surface 20 of the top panel 19. This will help stabilize the filter 27 at both ends prior to the critical movement of the tab A into the slot 56 as illustrated in FIG. 4. In this third alignment position, the tab A is supported on the surface 52 or tab C or surface 20 and is angularly displaced from the slot 56. The lever 63 is biased to the outward position and the switch 61 is in its open state. Further axial movement of the filter 27 is prevented by the misalignment of the tab C with respect to the slot 22 and the tab A with respect to the slot 56.

Figure 5:
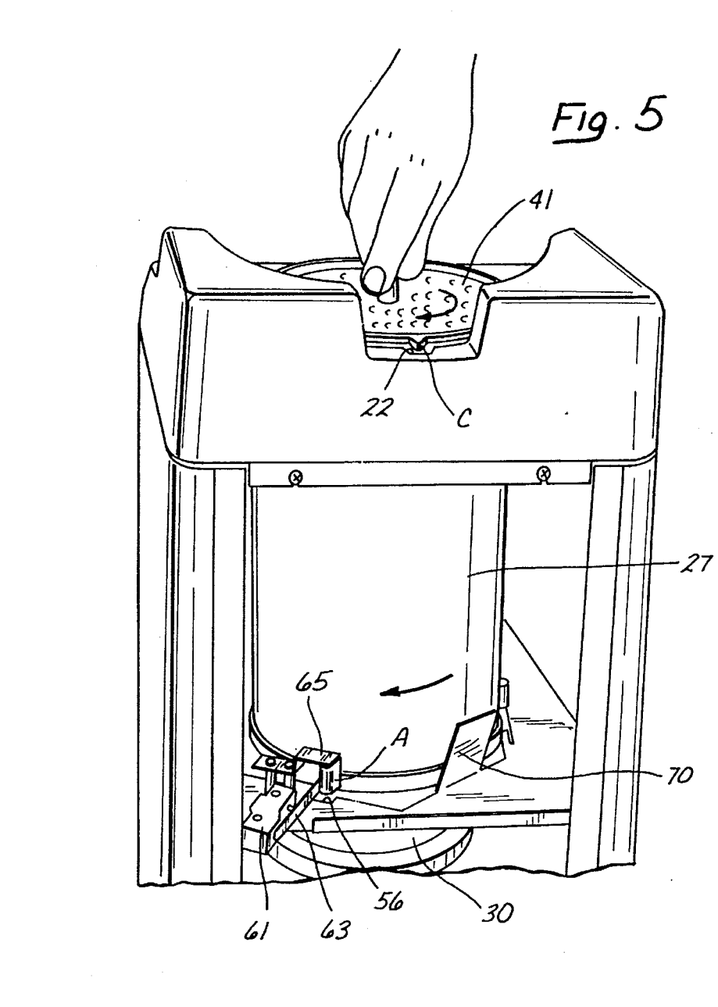
FIG. 5 is a perspective view of the evacuator and primary filter being rotated to a fourth alignment position.
Figure 6:
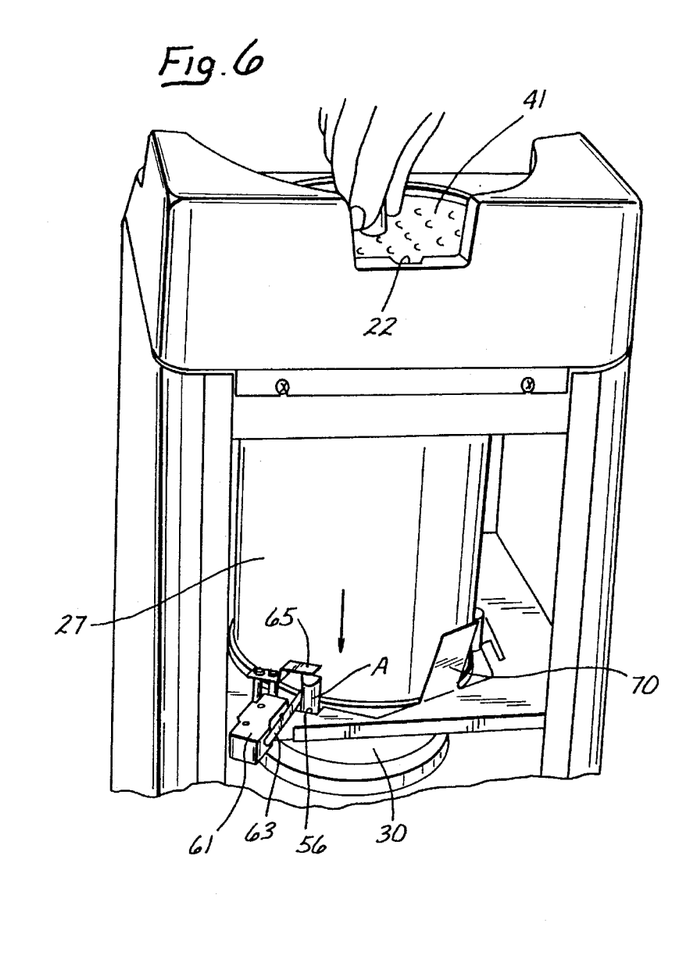
FIG. 6 is a perspective view of the evacuator with the primary filter disposed in its final operative position.

With angular rotation of the center post 42 these elements can be brought into alignment as illustrated in FIG. 5. As the tab A is angularly displaced, it moves into position over the slot 56 and beneath the locking flange 65. During this angular movement, the tab A contacts the lever 63 causing the switch 61 to move to its closed or "on" state. From this fourth alignment position illustrated in FIG. 5, the filter is free to drop further into the housing 12 to a final alignment position in the flow path 29 of the evacuator 10. In this final operative position illustrated in FIG. 6, the tab A continues to activate the switch 61. Importantly, the tab A and filter 27 are locked in this operative position. Axial movement of the filter 27 is prevented by the locking flange 65 which extends over the tab A, while angular movement of the filter 27 is prevented by the slots 56 and 22 which engage the tabs A and C, respectively.

Since the switch 61 is activated when the filter 27 is in its final operative position, the switch becomes an excellent vehicle for timing the amount of actual use to which the filter 27 has been exposed. When the evacuator 10 is activated, the switch 61 in its closed state can automatically activate a filter timer (not shown) in the top panel 19. This timer stays activated as long as the filter 27 is in place and the evacuator 10 is being used. Locking of the filter in its operative position is particularly desirable in order to inhibit any dislodgement of the filter during movement of the evacuator 10. The configuration including the locking flange 56 is particularly desirable for this purpose as it maintains the switch 61 in the closed state preventing resetting the memory associated with the filter timer.

Figure 7:
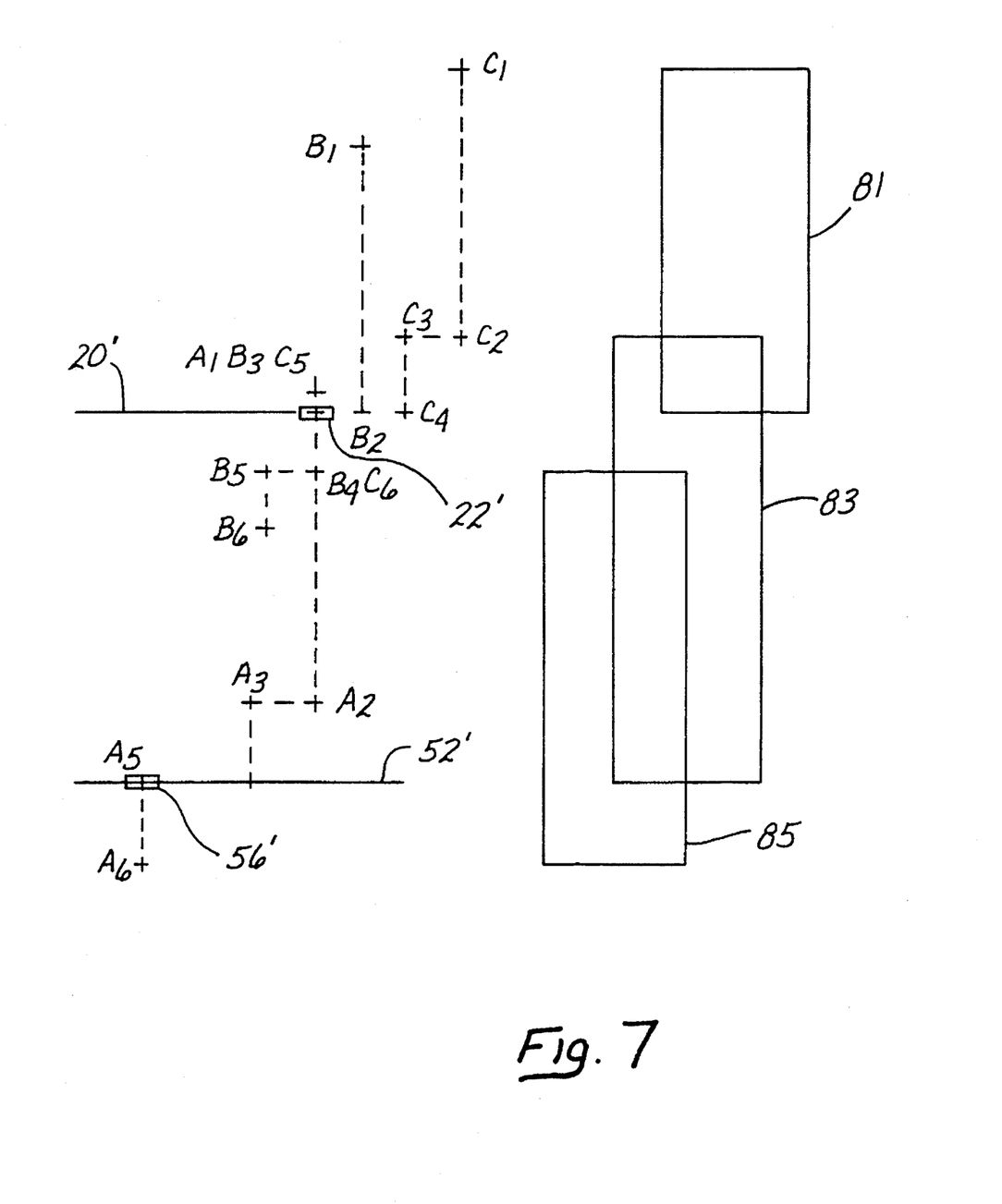
FIG. 7 is a schematic diagram of axial and rotational travel of the various tabs associated with the alignment of the primary filter.

The alignment apparatus associated with the tabs A, B, and C and the alignment slots 22 and 56 can be better understood with reference to the schematic of FIG. 7. In this schematic, the top surface 20 is represented by the line 20' and the surface 52 is illustrated by the line 52'. The alignment slots are designated by the reference numerals 22' and 56' respectively. The respective tabs A, B, and C are provided with subnumerals 1–6 which indicates the position of each tab at six different times in the alignment process. For example, in the initial alignment position illustrated in FIG. 2, tab A is disposed over the alignment slot 22. In the schematic of FIG. 7, the tab $A_1$ is shown at this time 1 to be aligned with the slot 22'. At the same time, the slots B and C are shown to be axially and angularly displaced at the positions $B_1$ and $C_1$ respectively. This initial alignment position is illustrated schematically and designated by the reference numeral 81 in FIG. 7.

From this position, the tab A drops axially through the slot 22 to a position and time designated $A_2$ in FIG. 7. At this time 2, the tab B is disposed on the surface 20' angularly displaced from the slot 22'. The tab C is disposed at the time and place indicated $C_2$. This second alignment position is designated by the reference numeral 83 in FIG. 7.

From this position, the filter 27 is angularly rotated to a time and location designated by the subnumeral 3. Thus the tab $B_3$ is brought into alignment with the slot 22' and the tabs A and C move respectively to the time and place designated $A_3$ and $C_3$. At this location, the filter 27 is again free to move axially to a time and place designated by the subnumeral 4. The tab B moves through the slot 22' to the position $B_4$ while the tabs A and C move into contact with the respective surfaces 52' or 20' as shown by the reference numerals $A_4$ and $C_4$ respectively.

Further angular movement of the filter 27 brings the tab C into alignment with the slot 22' and the tab A into alignment with the slot 56'. At this time, the tabs are designated $A_5$, $B_5$ and $C_5$. At this position, the filter is again free to drop axially to its final operative position designated by the reference numeral 85 in FIG. 7. Thus the tab A moves through the slot 56 and the tab C moves through the slot 22' to the respective positions $A_6$ and $C_6$.

Figure 8:
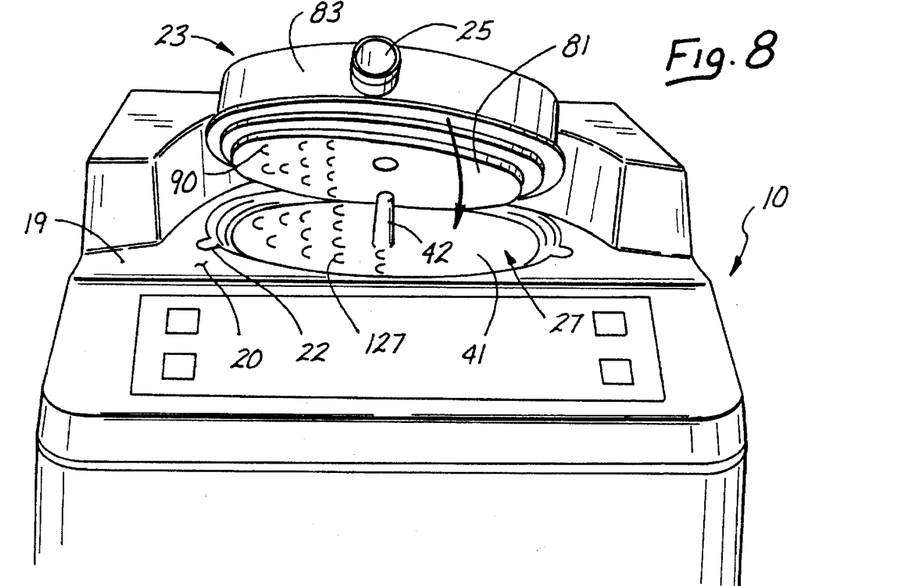
FIG. 8 is a perspective view of the front of the evacuator with the primary filter in place and the prefilter being mounted on the primary filter.
Figure 9:
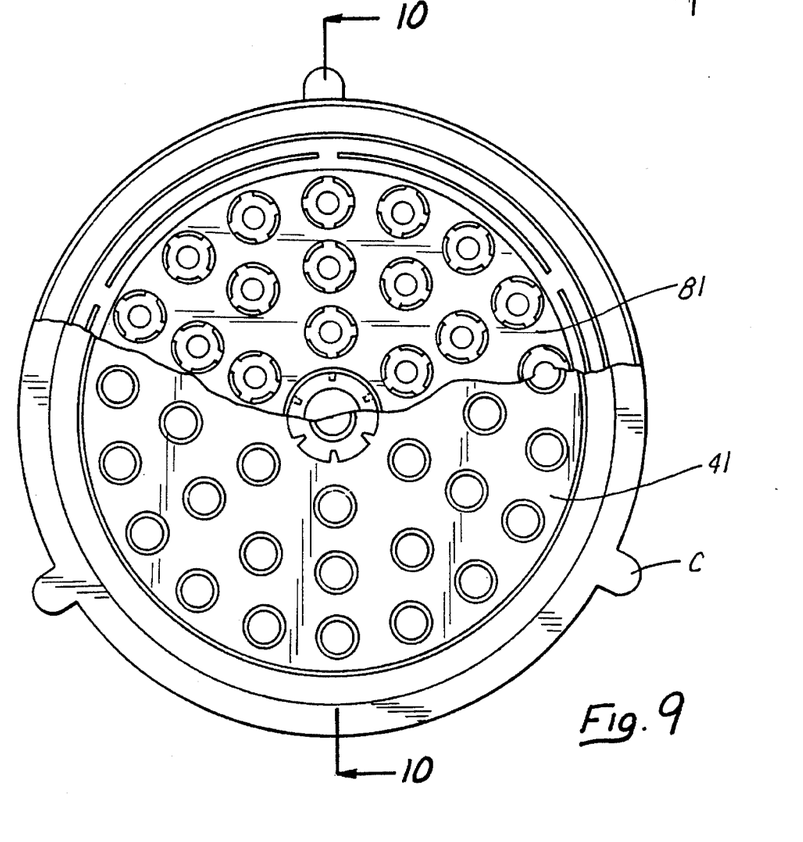
FIG. 9 is a top plan view of the lowest element of the prefilter partially removed to illustrated mating projection of the primary filter.
Figures 10, 11, 12:
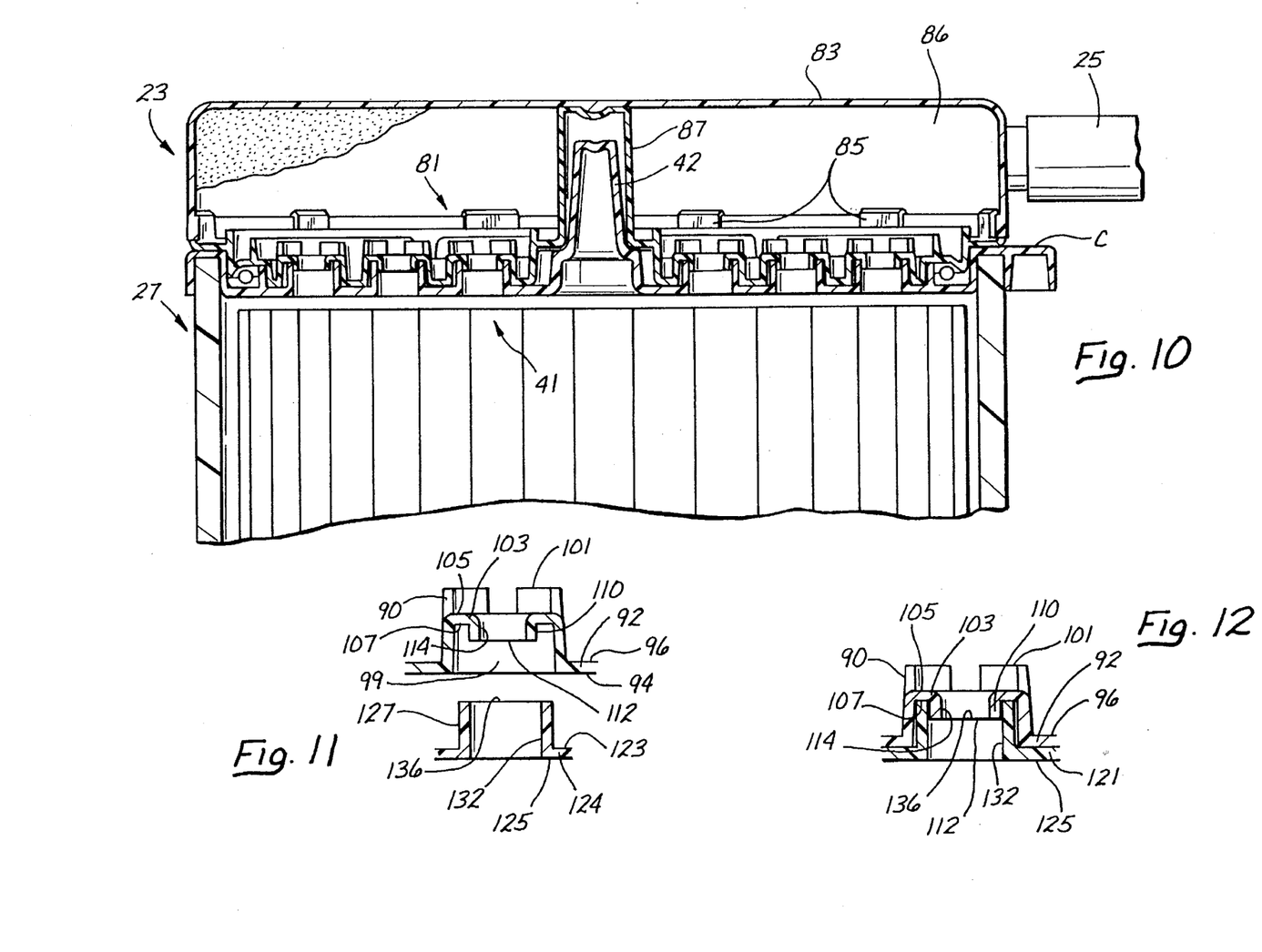
FIG. 10 is an axial cross section of the prefilter and primary filter taken along lines 10—10 of FIG. 9.
FIG. 11 is an enlarged cross-section view of interlocking projections on the prefilter and primary filter disposed in a separated relationship.
FIG. 12 is an enlarged cross-section view of the interlocking projections disposed in a mating relationship.

Another feature associated with the present invention relates to the alignment of the prefilter 23 on the primary filter 27. As best illustrated in FIGS. 8, 9 and 10 the prefilter 23 in one embodiment of the invention includes a bottom end wall 81 which can be fixed to a dome 86 by a plurality of snap tabs 85. The bottom wall 81 and the dome 83 are snap fit at the tabs 85 and together from a chamber 86 which initially receives the surgical smoke through the intake hose 25.

The end wall 81 of the prefilter 23 is configured to intimately engage the top end wall 41 of the primary filter 27. This is accomplished in a preferred embodiment wherein the end wall 81 includes a central cylinder 87 which is configured to receive the center post 42 of the primary filter 27.

The configuration of the bottom wall 81 of the prefilter 23 and the top wall 41 of the primary filter 27 is of particular interest, not only due to their interlocking configurations but also the advantages they provide in isolating a user from contaminated surfaces. The end wall 81 in a preferred embodiment includes a plurality of projections designated by the reference numeral 90 in FIG. 11. Each of the projections extends from a bottom wall 92 having a bottom surface 94 and a top surface 96. The projections 90 extend upwardly into the cavity 86 and include an outer cylinder 98 which extends upwardly from the top surface 96 to an inner surface 101. Along the length of the outer cylinder 98, a flange 103 extends radially inwardly and includes an inner surface 105 which is recessed from the surface 101 and an outer surface 107 which is recessed from the surface 94. An inner cylinder 110 extends downwardly from the flange 103 to an outer surface 112 which is also recessed from the surface 94. An axial bore 114 extends through the inner cylinder 110 and annular flange 103 to provide communication across the bottom wall 92.

A mating structure in the top wall 41 of the primary filter 27 includes a top wall 121 having an outer surface 123 and an inner surface 125. An upstanding cylinder 127 sized to fit between the outer cylinder 98 and the inner cylinder 110 extends upwardly from the surface 123 to an outer surface 136. An axial bore 132 extends through the cylinder 127 and provides communication across the top wall 121.

When the prefilter 23 is aligned with the primary filter 27, the cylinder 127 of the bottom end wall 38 registers with a respective recess 99 in the bottom end wall 81. In a specific embodiment, the outer surface 130 of the cylinder 127 is brought into relationship with the outer surface 107 of the annular flange 103. The surfaces 94 and 123 may or may not be in contact at this time. Importantly, when the cylinder 127 registers with the respective projection 90, the axial bore 114 extends into the axial bore 132 to provide communication across the respective walls 92 and 121. In addition, projections 90 are able to support a filter media which may be positioned on top.

With this orientation, the surgical smoke, which may have hazardous contaminants, will pass from the cavity 86 into the outer cylinder 98 contaminating the surfaces 101 and 105. From the outer cylinder 98, the smoke will enter the inner cylinder 110 contaminating the axial bore 114. The smoke will then flow into the cylinder 127 contaminating the surface 112 as well as the lower portion of the axial bore 132. It is of particular interest that the surfaces 94 of the bottom wall 92 and the surfaces 136 and 123 of the top end wall 41 remain uncontaminated. These surfaces represent the major surfaces which would normally be contacted by a user handling either the prefilter 23 or primary filter 27. Thus with the interlocking projections associated with these respective filters 23, 27, a user is isolated from any contaminants which may have been deposited on the filters 23, 27. It is of particular importance that the surface 114 and the surface 112 of the projections 90 which would normally be contaminated, are recessed from the surface 94.

It is desirable to configure the projections 90 so that the contaminated surfaces can not be easily reached with normal handling of the prefilter 23. As noted, these contaminated surfaces may include the surfaces 110, 112 and 114. In a preferred embodiment, the surface 112 which is closest to the outer surface 94 is recessed a distance about 3/16 inch. The inside diameter of the outer cylinder 90 has a diameter of about ½ inch. With these dimensions, the fingers of a user holding the filter 23 would typically be isolated from the contaminated surfaces. In addition, these multiple projections channel and distribute the smoke and contaminants within the filters.

From this detailed discussion it will be apparent that there are many other combinations of tabs and slots which can function to align the filter 27 as it is loaded into and removed from the evacuator 10. For example, the tabs A, B, and C might be replaced by a single tab extending along the entire length of the primary filter 27. Certainly other orientations and numbers of the tabs A, B, and C will now be apparent for other alignment configurations. Other systems and methods will now be apparent for achieving this alignment with access to only one end of the filter 27 while still providing a suitable degree of protection for fragile elements such as the switch 61 while maintaining the filter in a generally locked final operative position. It will also be apparent that the switch 21 can be activated by elements of the filter other than the tab A. Similarly, means for locking the cylinder in its final operative position, could function with respect to filter parts other than the tab A. Other forms of interlocking projections on the filters 23 and 27 will also be apparent for isolating a user from contaminated surfaces.

Given these wide variations, which are all within the scope of this concept, one is cautioned not to restrict the invention to the embodiments which have been specifically disclosed and illustrated, but rather encouraged to determine the scope of the invention only with reference to the following claims.

We claim:

1. A surgical smoke evacuator, comprising:

a housing;

means for defining an air flow channel through the housing;

at least one filter having an axis and an outer wall extending along the axis, the filter being sized and configured for placement in an operative position along the air flow channel;

a wall of the housing defining a filter cavity within the housing, the filter cavity being sized and configured to receive the at least one filter;

portions of the outer wall of the filter and the wall of the housing defining at least one slot extending along a circuitous path;

at least one tab extending from the other of the outer wall of the filter and the wall of the housing, the tab being sized and configured for sliding movement along the slot by lowering and rotating the filter relative to the housing so that the tab is moved along the slot in a predetermined sequence.

2. The smoke evacuator recited in claim 1 further comprising:

a switch disposed in a housing and being operable to permit activation of the smoke evacuator; and the at least one tab being disposed to extend from the outer surface of the filter to operate the switch when the filter is disposed in the operative position in the filter cavity.

3. The smoke evacuator recited in claim 2 further comprising means disposed relative to the one tab for inhibiting axial movement of the filter when the filter is operatively positioned in the filter cavity.

4. The smoke evacuator recited in claim 1 wherein the one filter is a first filter and the smoke evacuator further comprises:

an end wall of the first filter having a plurality of projections extending outwardly of the first filter;

a second filter;

an end wall of the second filter having a plurality of recesses extending inwardly of the second filter; and the projections of the first filter matting with the recesses of the second filter in a telescoping relationship to support the second filter on the first filter.

5. The smoke evacuator recited in claim 1 wherein the portions defining the at least one slot include:

first portions defining a first region of the slot, the first portions extending generally axially of the filter; and second portions defining a second region of the slot, the second region extending generally angularly of the filter.

6. The smoke evacuator recited in claim 5 further comprising:

third portions of the slot extending between the first portions of the slot and second portions of the slot, the third portions engaging the at least one tab and providing tactile feedback facilitating a transition of the sliding movement of the filter between the lowering of the filter and the rotating of the filter in the predetermined sequence.

7. The surgical smoke evacuator recited in claim 1, where in the slot defining portions and the at least one tab provide for alignment of the filter relative to the housing at a first position at the inlet, and at a second position within the housing, the second position being axially disposed and angularly displaced from the first position, the evacuator further comprising means for inhibiting axial movement of the filter in the second position.

8. The surgical smoke evacuator recited in claim 1, wherein the housing includes a first supporting surface;

the at least one tab is a first tab extending from the outer wall of the filter; and the first tab is in contact with the first supporting surface when the filter is in the first position.

9. A filter adapted for insertion along an air flow path in a surgical smoke evacuator having a filter inlet, a filter cavity, and a slot extending therebetween along a circuitous path, the filter comprising:

a top end wall forming an inlet of the filter;

a bottom end wall opposing the top end wall and forming an outlet of the filter;

a side wall having an axis and extending between the top end wall and the bottom end wall, the side wall forming with the top end wall and the bottom end wall an enclosure of the filter;

a filter medium disposed in the enclosure for filtering contaminants from the air flow path;

a plurality of tabs each extending laterally from an associated one of the side wall and the end walls, the tabs being positioned for alignment with the slot of the evacuator as the filter is lowered and rotated in a predetermined sequence through the filter inlet and into the filter cavity;

a top wall included in the top end wall of the filter and extending transverse to the axis of the sidewall; and a plurality of projections included in the top end wall, each of the projections extending from the top wall and defining an inlet passage communicating with the filter cavity, the projections collectively forming at least a portion of the inlet of the filter.

10. The filter recited in claim 9 further comprising:

a center post included in the top end wall and extending axially outwardly of the top wall, the center post being rotatable to rotate the filter about the axis and along the circuitous path.

* * * * *